US009916650B2

United States Patent
Engel

(10) Patent No.: US 9,916,650 B2
(45) Date of Patent: Mar. 13, 2018

(54) IN-PROCESS FAULT INSPECTION USING AUGMENTED REALITY

(71) Applicant: AIRBUS DEFENCE AND SPACE GMBH, Ottobrunn (DE)

(72) Inventor: Franz Engel, Munich (DE)

(73) Assignee: Airbus Defence and Space GmbH, Taufkirchen (DE)

( * ) Notice: Subject to any disclaimer, the term of this patent is extended or adjusted under 35 U.S.C. 154(b) by 223 days.

(21) Appl. No.: 14/883,001

(22) Filed: Oct. 14, 2015

(65) Prior Publication Data
US 2016/0104276 A1    Apr. 14, 2016

(30) Foreign Application Priority Data

Oct. 14, 2014 (EP) .................................. 14003513

(51) Int. Cl.
| | | |
|---|---|---|
| G06K 9/00 | (2006.01) | |
| G06T 7/00 | (2017.01) | |
| G06T 19/00 | (2011.01) | |
| G01N 21/88 | (2006.01) | |
| G01N 21/95 | (2006.01) | |

(52) U.S. Cl.
CPC ....... *G06T 7/0004* (2013.01); *G01N 21/8851* (2013.01); *G01N 21/9515* (2013.01); *G06T 19/006* (2013.01); *G01N 2021/8893* (2013.01); *G06T 2207/30164* (2013.01)

(58) Field of Classification Search
CPC ............ G01N 21/9501; G01N 21/9505; G06T 7/0004; G06T 2207/30148

USPC ....... 382/141, 145, 147, 149, 152, 209, 278; 348/86, 125

See application file for complete search history.

(56) References Cited

U.S. PATENT DOCUMENTS

| | | | | |
|---|---|---|---|---|
| 6,603,541 | B2 * | 8/2003 | Lange ..................... | G01N 21/47 356/237.2 |
| 6,636,581 | B2 * | 10/2003 | Sorenson ............... | G01N 23/04 378/58 |
| 7,127,098 | B2 * | 10/2006 | Shimoda .......... | G01N 21/95684 250/208.1 |
| 7,508,971 | B2 * | 3/2009 | Vaccaro ................. | G01B 5/008 382/141 |
| 7,602,482 | B2 * | 10/2009 | Matsui ................... | G01N 21/47 356/237.3 |

(Continued)

FOREIGN PATENT DOCUMENTS

| | | |
|---|---|---|
| DE | 102005025470 A1 | 12/2006 |
| DE | 102009008039 A1 | 7/2010 |
| EP | 1810816 A2 | 7/2007 |

OTHER PUBLICATIONS

European Search Report for EP14003513 dated Apr. 28, 2015.
(Continued)

*Primary Examiner* — Yosef Kassa
(74) *Attorney, Agent, or Firm* — Jenkins, Wilson, Taylor & Hunt, P.A.

(57) ABSTRACT

An arrangement for visual fault inspection of at least one component includes a fault identification unit for identifying a structural fault of the component and for determining at least one piece of fault information, and an overlay device connected to the fault identification unit, configured for context-dependent overlay of the fault information in a component image in real-time.

13 Claims, 3 Drawing Sheets

(56) References Cited

U.S. PATENT DOCUMENTS

| | | | |
|---|---|---|---|
| 7,796,801 B2* | 9/2010 | Kitamura | G06K 9/00 348/125 |
| 7,835,567 B2 | 11/2010 | Oldani | |
| 7,940,385 B2* | 5/2011 | Hamamatsu | G01N 21/9501 356/237.1 |
| 7,973,922 B2* | 7/2011 | Matsui | G01N 21/47 356/237.3 |
| 8,045,785 B2* | 10/2011 | Kitamura | G06K 9/00 348/125 |
| 8,318,240 B2* | 11/2012 | Zapalac | H01L 31/0392 29/402.09 |
| 8,355,123 B2* | 1/2013 | Hamamatsu | G01N 21/9501 356/237.1 |
| 8,545,030 B2* | 10/2013 | Anderson | B32B 27/06 359/485.01 |
| 2007/0173966 A1 | 7/2007 | Oldani | |
| 2011/0017381 A1 | 1/2011 | Oldani | |

OTHER PUBLICATIONS

English Abstract of DE102005025470, Publication Date: Dec. 7, 2006.
English Abstract of DE102009008039, Publication Date: Jul. 1, 2010.

* cited by examiner

IN-PROCESS FAULT INSPECTION USING AUGMENTED REALITY

FIELD OF THE INVENTION

The invention relates to an arrangement for visual fault inspection of at least one component, in particular an aircraft component, during the component production process. The invention also relates to a corresponding method for visual fault inspection of the component.

BACKGROUND OF THE INVENTION

In aviation manufacturing, a very large amount of work still continues to be performed manually by suitably qualified personnel. This is problematic particularly for a fibre composite construction because fibre composite materials such as carbon fibre reinforced plastics (CFRP) are inherently very expensive and the manufacturing costs are increased further by the manual labour. This prohibits or at least reduces technologically advantageous fields of application of fibre composite materials.

AFP (automated fibre placement) technology solves this problem by using a fully automated manufacturing process for composite components. This technology places robot-guided fibre-reinforced plastics strips along a defined path on a three-dimensional tool surface using pressure and temperature. With this technology, the component is constructed from carbon fibre tapes applied tape by tape, i.e. layer by layer. The usual procedure for inspecting the quality is for a member of staff to examine the component for quality shortfalls after every layer. It is vital to avoid errors in the position of the tapes, even errors of just a few millimeters, for instance 2 mm. Various error patterns can also arise during placement, for instance too large a distance between tapes, overlapping tapes, twisted tapes, tapes that have been pulled out or severed, tapes joined together (splice), etc. Hence for large components, inspection is extremely time-consuming and error-prone. Since CFRP is inherently a black material, it is very hard to ascertain or detect the existence of gaps, which equate to a defect.

Implementing an automated quality assurance system (QAS), which ascertains production faults during the AFP production process of CFRP components, is known from the prior art. U.S. Pat. No. 8,668,793 B1 describes, for example, using an optical camera system for in-process fault identification and using a laser projector for fault indication. This system is used to identify and record defects during the production process. Nevertheless, the member of staff must subsequently still inspect the recorded faults personally and, if applicable, consult an expert such as a structural load specialist in order to assess the implications of the defect.

SUMMARY OF THE INVENTION

It is one idea of the invention to provide an arrangement and a method which each at least reduce the above-mentioned problem or problems.

The arrangement according to the invention comprises a fault identification unit for identifying a structural fault of the component and for determining at least one item of fault information, and comprises an overlay device connected to the fault identification unit for context-dependent overlay of the fault information in a component image in real-time.

The overlay device may be any means for context-dependent overlay of the fault information in a component image in real time, and may in this case correspond to an augmented reality system which enhances the visual inspection of the component. The user of the arrangement can use these means to identify the structural defects and the fault information directly and easily.

One advantage of the solution according to the invention is that the arrangement provides a clear overall view of the component, this component image being provided with additional information and allowing faster and more precise inspection.

The arrangement according to the invention is suitable for visual fault inspection of an aircraft component during the production process, which component to be examined is advantageously made of carbon fibre reinforced plastics (CFRP). In this arrangement, the fault identification unit comprises at least one sensor module, which during the component production process can detect the existence of defects in adjacent carbon fibre tapes and/or determine the size of the defects or can specify the amount of carbon fibre tapes. The fault identification unit may be part of a quality assurance system, for example. The structural defect in this context means a gap situated between the carbon fibre tapes or a crack or a fissure or the like.

The overlay device may in particular comprise a position-finding unit for determining exact information about the position of the component and the position of the user. The overlay device may also comprise a processor unit connected to the fault identification unit and to the position-finding unit, adapted for processing the information determined by the fault identification unit and position-finding unit and for integrating the processed information in a component image. The overlay device may further comprise a visualisation unit connected to the processor unit, adapted for displaying the component image containing the integrated information.

The various units of the arrangement according to the invention, i.e. the fault identification unit, the position-finding unit, the processor unit and the visualisation unit, can be connected to one another by cables or wirelessly, either entirely or in part. Thus, the data or information can be transmitted wirelessly. It is also possible to integrate some of these units in other units. For instance, the processor unit can be integrated in the visualisation unit, and can correspond to a portable visual aid.

The position-finding unit or tracking system is used here to acquire the exact orientation and position of the component. The ascertained fault information can hence be laid over the component in real time, and using the visualisation unit can be identified to the user. The position-finding unit can operate on an optical basis. In this case, optical cameras for capturing the surrounding area can be used, with landmarks being used for orientation. The landmarks can here be natural features such as e.g. the tip of the nose or corner of the eye, but may also be man-made. Man-made landmarks may comprise LEDs that flash at regular intervals or battery-operated markers that have no cabling.

Alternatively, the system can find its position on the component itself by comparing component features, which are detected by a portable camera for example, with the target data.

Orientation can also be performed using electromagnetic or ultrasound signals or mechanical elements.

The visualisation unit here corresponds to a visual aid for the user, which speeds up component inspection significantly. Hence the user no longer needs to locate on the component the fault or defect identified by the fault identification unit, because all the necessary fault information is provided in real time in the component image displayed by the visualisation unit. In addition, the information about the component position is integrated with the component image, allowing the user to locate the correct position of the structural fault on the component very quickly.

In one embodiment of the invention, the overlay device may comprise a capture unit for capturing the component image. This unit may be a photo camera or a video camera, which may be separate from the visualisation unit or an integral part thereof.

The arrangement can use the capture unit to capture the real component and can use the processor unit to process the image, for example in order to highlight the structural faults by a change in size or using colour, and can use the visualisation unit to display to the user the modified but photo-realistic image.

Alternatively, the overlay device can use a purely computer-generated virtual component image, with the relevant identifiers for the faults being displayed in the correct position in the component image.

In this context, the user can scan a virtual component (in its original size) in an open area, where the component may be purely virtual or can be overlaid by photos or optically scanned images of the original component. The user can hence safely inspect the component while the machine is still operating. This means, for example, that an inspector can reliably meet repair requirements, and a second machine can be used, which repairs the damage to the component while the production process is still in progress.

In a particular embodiment of the invention, the capture unit may be an on-board camera, in which case the image corresponds to a real-time image of the component.

In one embodiment of the invention, the visualisation unit may comprise a portable computer such as a smartphone or tablet, for example, which can be pointed directly at the component to be examined. In an alternative embodiment of the invention, the visualisation unit may comprise a head-mounted display such as eyeglasses or a helmet-mounted display for example. It is also possible to use contact lenses or bionic contact lenses or implants or targeted stimulation of parts of the brain or of the optic nerve (to generate images in the head), which comprise a built-in display element that includes an integrated circuit, LEDs and an antenna for wireless communication. In another alternative embodiment of the invention, the visualisation unit may comprise an optical projector or a portable screen or a portable transparent display.

It is also possible to use a display comprising at least one camera in order to record the real world and for the display to reproduce an augmented view of this world, with an image containing integrated augmented information being projected by the display or reflected on the display.

In one embodiment of the invention, the fault information contains the pinpointing or coordinates of the structural fault. It is thus easy to immediately or retrospectively locate the fault or defect in the component.

Alternatively or additionally, the fault information can comprise the severity of the structural fault. The user can thereby identify a fault as uncritical, critical, irreparable etc. and if applicable initiate suitable actions by means of the arrangement.

The visualisation unit can comprise a touchscreen display so that the user can activate certain functions by touching the screen. For instance, it is possible to touch a fault or icon shown on the display in order to assign a repair to be performed to the relevant technician, or simply to facilitate a telephone call to the technician.

In another embodiment of the invention, the position-finding unit may comprise reference markers for calculating the component position. The arrangement can thereby locate itself with respect to the position of the component. It is also possible here, however, to use an external signal such as a GPS signal, for example, or a position measuring instrument to determine the component position.

The processor unit can comprise a synchronising unit in order to synchronise the movement of the visualisation unit and/or the direction of view of the visualisation unit with the displayed component image. In other words, when the user points the arrangement according to the invention at the component, the component image also moves according to the movement and direction of view of the visualisation unit. The structural faults and the corresponding fault information are displayed in the component image. Hence the user can approach the component and scan it, while receiving a correctly positioned display of the previously measured or identified faults for each view of the component. This speeds up considerably the process of locating individual component faults.

In yet another embodiment of the invention, the visualisation unit comprises means for pinpointing the structural faults on the displayed component image. Hence the arrangement can use virtual arrows, such as those used in a navigation device, to guide the user to the relevant fault locations.

The method according to the invention for visual fault inspection of a component comprises identifying a structural fault on the component and determining at least one item of fault information using a fault identification unit, and the context-dependent overlay of the at least one item of fault information in a component image in real-time.

This method can be used to enhance a scheduled fault inspection of a component. With no indication of possible defects, the user approaches the component and using the method according to the invention obtains information about the currently viewed component image, for example information such as the exact position of a gap or the size of this gap.

The method step of context-dependent overlay of the fault information in a component image in real time may in particular comprise determining exact information about the position of the component and the position of the user by means of a positioning-finding unit. In addition, the method may comprise processing the fault information and information about the position of the component and the position of the user and integrating the processed information in a component image by means of a processor unit, and displaying the component image containing the integrated information by means of a visualisation unit.

In one embodiment of the invention, the image can be captured by a capture unit, in particular in real-time.

In another embodiment of the invention, the displayed component image moves according to the movement of the visualisation unit and/or the direction of view of the visualisation unit.

In another embodiment of the invention, processing the fault information comprises categorising the structural fault and, if applicable, initiating countermeasures. Hence the user can assess the imperfection and, if applicable, take countermeasures, directly at the measurement location. In addition, the fault position can be saved.

By virtue of this method, the user can be guided directly and easily to the structural fault or to the defect, both for faults that are at close proximity but very small and hence invisible and at a large distance from the component.

The method according to the invention also makes it possible locally to display additional information, for example information about defects in underlying layers and about the size of the fault, and to categorise the fault and initiate counter measures.

BRIEF DESCRIPTION OF THE DRAWINGS

Advantages and practical aspects of the present invention also appear in the following description of selected embodiments with reference to the figures, in which.

DETAILED DESCRIPTION OF EMBODIMENTS OF THE INVENTION

Figure 1:
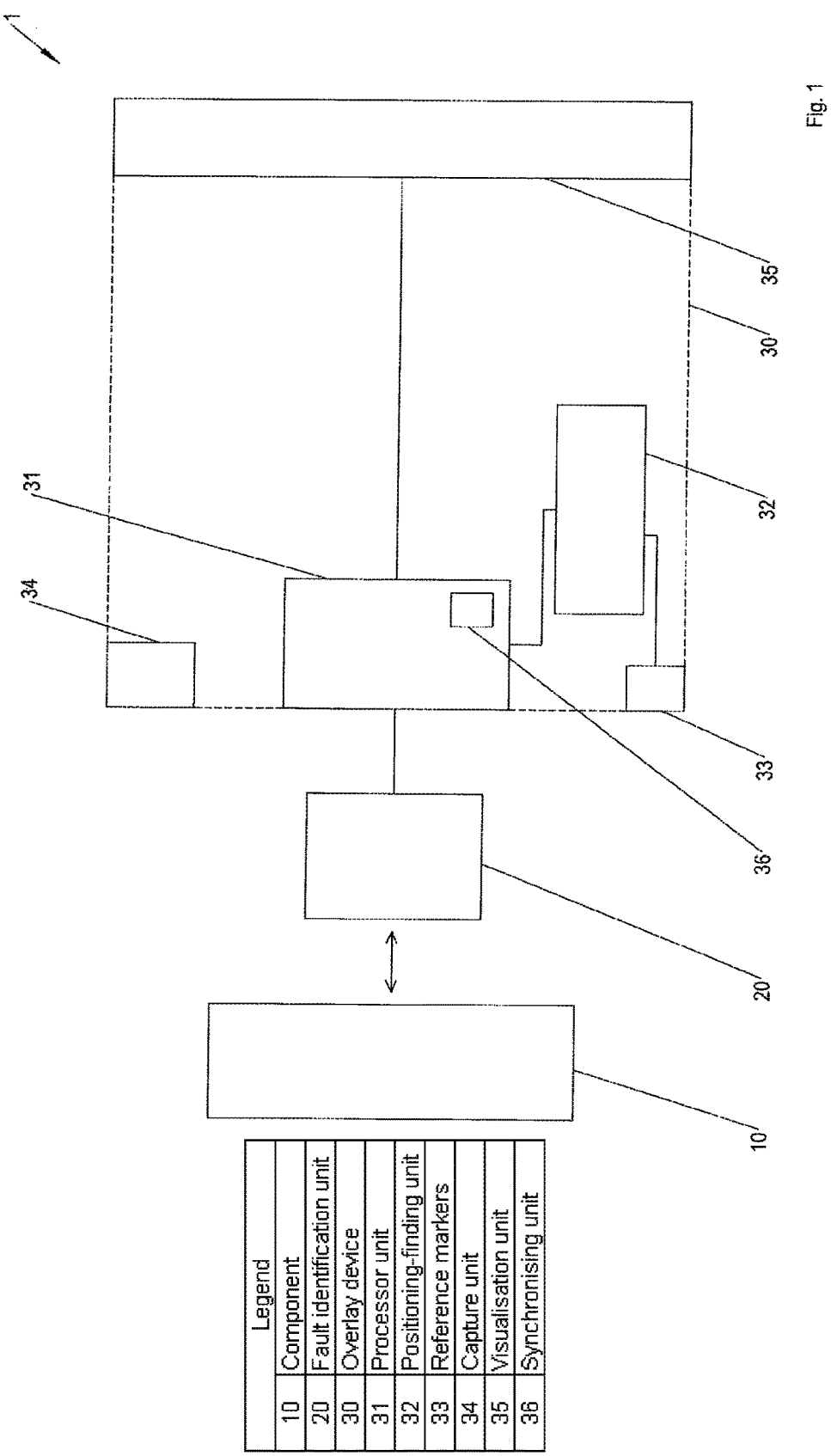
FIG. 1 is a schematic diagram of the arrangement according to an embodiment of the invention.

FIG. 1 describes an arrangement 1 for visual fault inspection of a component 10, in particular an aircraft component. The arrangement 1 comprises a fault identification unit 20, which optically examines the surface of the component 10 in order to detect structural faults. The component 10 comprises carbon fibre tapes, the fault identification unit 20 performing a fault inspection during the AFP production process of the component 10. The fault identification unit 20 collects the fault information (position and size of the defect) and transmits this information to means 30 for context-dependent overlay of the fault information in a component image B in real time. The means 30 comprise a processor unit 31 and a position-finding unit 32, which is connected to the processor unit 31 and uses suitable reference markers 33 to determine the exact position of the component 10 and of the user. The processor unit 31 processes the fault information and the information determined by the positioning-finding unit 32, and integrates this information in a component image B. The image is captured here by a capture unit 34 connected to the processor unit 31. The processed component image B is then transmitted by the processor unit 31 to a visualisation unit 35 and hence displayed to the user. The processor unit 31 also comprises a synchronising unit 36 in order to be able to synchronise the movement of the visualisation unit 35 and/or the direction of view of the visualisation unit 35 with the displayed component image B.

Figure 2:
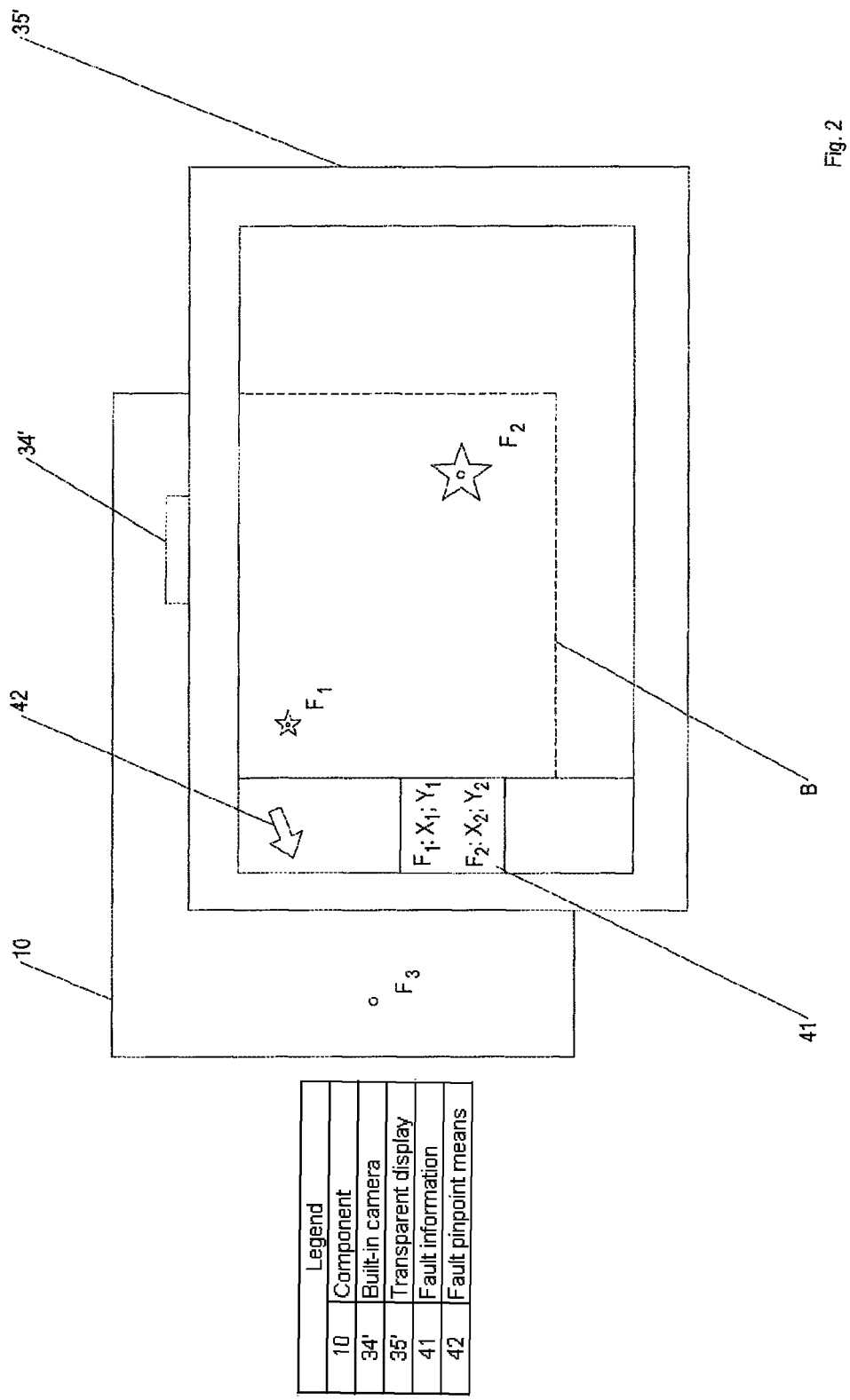
FIG. 2 is a schematic diagram of the visualisation unit according to a further embodiment of the invention.

FIG. 2 describes a visualisation unit according to an embodiment of the invention. In this embodiment, the visualisation unit corresponds to a transparent portable display 35' having a built-in camera 34', which communicates wirelessly with a processor unit 31 (not shown in FIG. 2). The transparent display 35' is pointed at the component 10 and shows a processed image B of the component 10 in real time, in which fault information 41 is displayed by means of identified and indicated faults $F_1$, $F_2$. The fault information 41 is detected by a fault identification unit 20 (not shown in FIG. 2), processed by a processor unit 31 and transmitted wirelessly to the display 35'. This Information 41 corresponds in particular to the coordinates $X_1$, $Y_1$; $X_2$, $Y_2$ of the indicated faults $F_1$, $F_2$. The display 35' also comprises means 42 for pinpointing a fault $F_3$, which fault $F_3$ is not indicated on the display 35'. These means are represented by an arrow 42 in order to inform the user about the position of an additional fault $F_3$, which is not indicated in the display 35', and/or to guide the user to this fault $F_3$. The faults $F_1$, $F_2$ indicated on the display 35' are moreover represented by a symbol (a star) of various sizes. The size of the symbol here corresponds to the severity of the fault $F_1$, $F_2$, for example the size of a gap; the larger the symbol the larger or more severe the defect.

Figure 3:
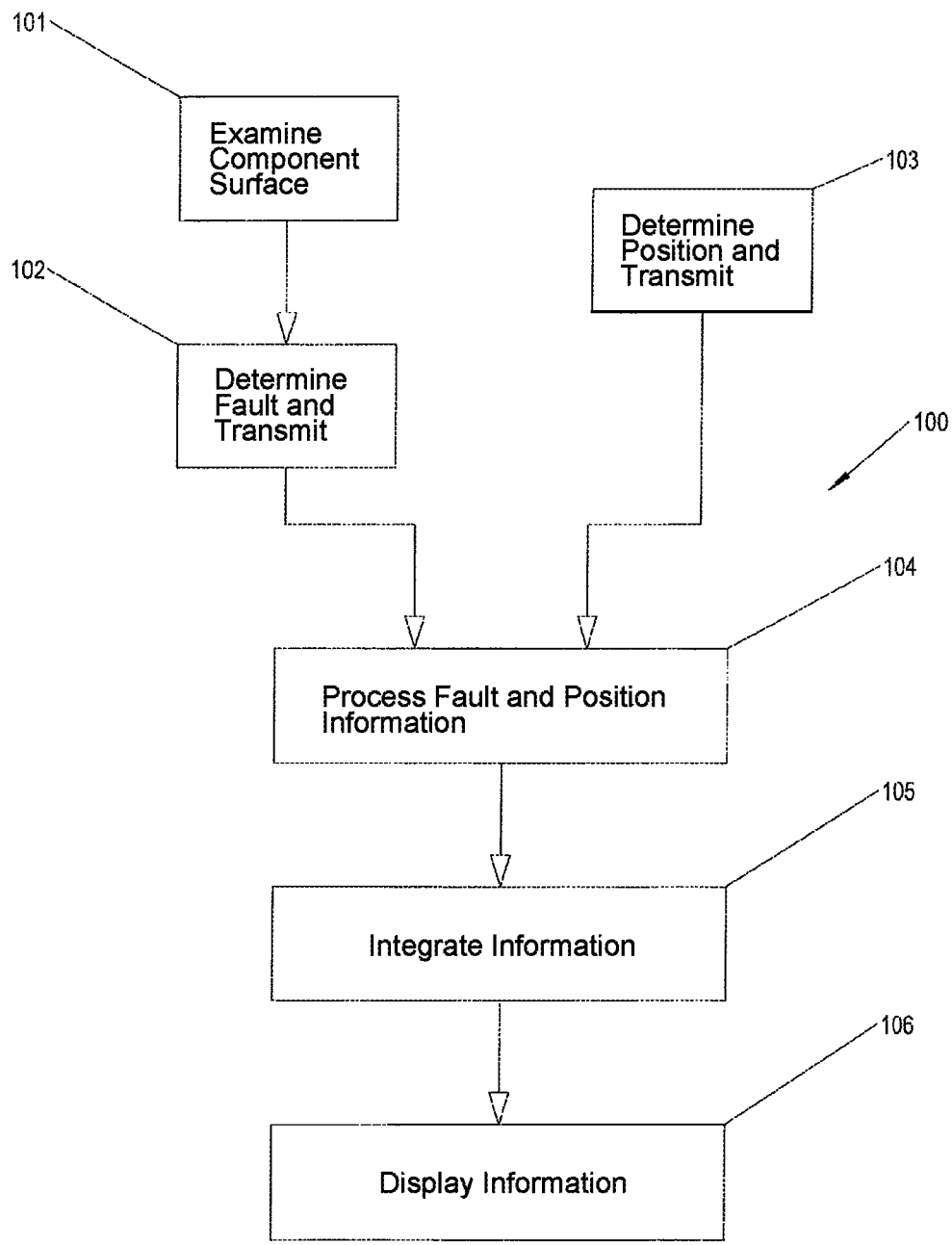
FIG. 3 is a flow diagram of a method according to another embodiment of the invention.

FIG. 3 describes the method 100 for visual fault inspection of an aircraft component 10 during the production process, which component 10 to be examined is made of carbon fibre reinforced plastics. As the first step 101, the surface of the component 10 is examined in order to identify structural faults or defects of the component 10. Then in the step 102, fault information, for example about the size of the defect and/or the position thereof, is determined and transmitted to a processor unit 31. Simultaneously, in the step 103, information about the position of the component 10 and of the user is determined and likewise transmitted to the processor unit 31. In the step 104, the processor unit 31 process the information determined by the fault identification unit 20 and by the positioning-finding unit 32. In this case, the faults are categorised on the basis of the size of the defect for example. In the step 105, the information determined above is integrated in a component image B, and this is displayed to the user in the step 106.

The embodiment of the invention is not restricted to the examples described above and the highlighted aspects but can also have numerous different variations that are routine in the art.

An arrangement is disclosed for visual fault inspection of at least one component, which arrangement comprises a fault identification unit for identifying a structural fault of the component and for determining at least one piece of fault information, and comprises means, which are connected to the fault identification unit, for context-dependent overlay of the fault information in a component image in real-time.

Without further elaboration, it is believed that one skilled in the art can, using the preceding description, utilize the present invention to its fullest extent. The preceding preferred specific embodiments are, therefore, to be construed as merely illustrative, and not limitative of the remainder of the disclosure in any way whatsoever.

The entire disclosures of all applications, patents and publications, cited herein and of corresponding European application No. 14003513.0, filed Oct. 14, 2014 are incorporated by reference herein.

From the foregoing description, one skilled in the art can easily ascertain the essential characteristics of this invention and, without departing from the spirit and scope thereof, can make various changes and modifications of the invention to adapt it to various usages and conditions.

What is claimed is:

1. An arrangement for visual fault inspection of at least one component, comprising:
  a fault identification unit configured to identify a structural fault in the component and to determine at least one item of fault information;
  an overlay device connected to the fault identification unit and configured to overlay the at least one item of fault information in a context-dependent manner in a component image in real-time,
  a positioning-finding unit configured to determine exact positioning information about a position of the component and about a position of the user;
  a processor unit connected to the fault identification unit and to the position-finding unit, the processor unit being configured to process the at least one item of fault information and the positioning information and to integrate the processed information in the component image; and a visualisation unit connected to the processor unit configured to display the component image containing the integrated information of the processor unit.

2. The arrangement according to claim 1, further comprising:

a capture unit connected to the processor unit and configured to capture the component image.

3. The arrangement according to claim 1, wherein the component image corresponds to a real-time image of the component.

4. The arrangement according to claim 1, wherein the visualisation unit comprises one of a portable computer, eyeglasses, contact lenses, a portable screen, and a portable transparent display.

5. The arrangement according to claim 1, wherein the at least one item of fault information comprises pinpointing or coordinates of the structural fault.

6. The arrangement according to claim 1, wherein the at least one item of fault information comprises the severity of the structural fault.

7. The arrangement according to claim 1, wherein the positioning-finding unit comprises reference markers for calculating the position of the component and of the user.

8. The arrangement according to claim 1, wherein the processor unit comprises a synchronising unit configured to synchronise the movement of the visualisation unit and/or the direction of view of the visualisation unit with the displayed component image.

9. The arrangement according to claim 1, wherein the visualisation unit is configured for pinpointing the structural fault on the displayed component image.

10. A method for visual fault inspection of a component, the method comprising:

identifying a structural fault on the component;

determining at least one item of fault information of the structural fault using a fault identification unit;

overlaying the at least one item of fault information in context-dependent manner in a component image in real-time;

determining exact information about a position of the component and a position of the user by a positioning-finding unit;

processing the fault information and the information about the position of the component and the position of the user;

integrating the processed information in a component image by a processor unit; and displaying the component image containing the integrated information by a visualisation unit in real-time.

11. The method according to claim 10, wherein the component image is captured in real time.

12. The method according to claim 10, wherein the displayed component image moves according to the movement of the visualisation unit and/or the direction of view of the visualisation unit.

13. The method according to claim 10, wherein the processing of the fault information comprises:

categorising the structural fault;

determining whether countermeasures are necessary; and initiating counter measures depending on the determination.

* * * * *